(12) United States Patent
Jiang et al.

(10) Patent No.: US 11,786,682 B2
(45) Date of Patent: Oct. 17, 2023

(54) END-EXPIRATORY $CO_2$ GUIDED TRACHEAL INTUBATION DEVICE

(71) Applicant: Shanghai Ninth People's Hospital, Shanghai Jiao Tong University School of Medicine, Shanghai (CN)

(72) Inventors: Hong Jiang, Shanghai (CN); Ming Xia, Shanghai (CN); Yu Sun, Shanghai (CN); Jia Yan, Shanghai (CN)

(73) Assignee: Shanghai Ninth People's Hospital, Shanghai Jiao Tong University School of Medicine, Shanghai (CN)

(*) Notice: Subject to any disclaimer, the term of this patent is extended or adjusted under 35 U.S.C. 154(b) by 314 days.

(21) Appl. No.: 17/118,613

(22) Filed: Dec. 11, 2020

(65) Prior Publication Data

US 2021/0178097 A1    Jun. 17, 2021

(30) Foreign Application Priority Data

Dec. 11, 2019   (CN) .......................... 201911267307.7

(51) Int. Cl.
  *A61M 16/04* (2006.01)
  *A61M 16/00* (2006.01)

(52) U.S. Cl.
  CPC .... *A61M 16/0463* (2013.01); *A61M 16/0003* (2014.02); *A61M 16/045* (2014.02); *A61M 16/0488* (2013.01); *A61M 2016/0413* (2013.01)

(58) Field of Classification Search
  CPC .............. A61M 16/0003; A61M 16/04; A61M 16/0402; A61M 16/0434; A61M 16/045; A61M 16/0463; A61M 16/0477; A61M 16/0486; A61M 16/0488; A61M 2016/0413; A61M 2210/1032; A61M 2230/40

See application file for complete search history.

(56) References Cited

U.S. PATENT DOCUMENTS

| 4,244,362 A * | 1/1981 | Anderson ......... A61M 16/0418 128/207.14 |
| 8,382,908 B2 * | 2/2013 | Vazales .................. A61B 1/126 134/8 |
| 2004/0000314 A1 * | 1/2004 | Angel ................. A61M 16/042 128/207.14 |

(Continued)

*Primary Examiner* — Colin W Stuart
*Assistant Examiner* — Matthew D Ziegler
(74) *Attorney, Agent, or Firm* — JCIP GLOBAL INC.

(57) ABSTRACT

An end-expiratory $CO_2$ guided tracheal intubation apparatus includes: an intubation tube, an end-expiratory $CO_2$ catheter, a suction tube, an airbag and an inflation tube. The end-expiratory $CO_2$ catheter partially penetrates the sidewall of the intubation tube, one end of the end-expiratory $CO_2$ catheter extends beyond an end of the intubation tube, and the other end is connected to an end-expiratory $CO_2$ sensor, the suction tube partially penetrates a sidewall of the intubation tube, one end of the liquid suction tube extends beyond an end of the intubation tube, the other end is connected to an air pump, the airbag sleeves the outer wall of the intubation tube, the inflation tube partially penetrates the sidewall of the intubation tube, one end thereof is connected to the airbag, and the other end is connected to the air supply device.

2 Claims, 4 Drawing Sheets

(56) References Cited

U.S. PATENT DOCUMENTS

| | | | | |
|---|---|---|---|---|
| 2011/0315147 A1* | 12/2011 | Wood | ............... | A61M 39/105 |
| | | | | 128/207.15 |
| 2017/0232215 A1* | 8/2017 | Zannis | ............ | A61M 16/0493 |
| | | | | 128/207.14 |

* cited by examiner

END-EXPIRATORY CO₂ GUIDED TRACHEAL INTUBATION DEVICE

CROSS-REFERENCE TO RELATED APPLICATION

This application claims the priority benefit of China application serial no. 201911267307.7, filed on Dec. 11, 2019. The entirety of the above-mentioned patent application is hereby incorporated by reference herein and made a part of this specification.

TECHNICAL FIELD

The present invention relates to the technical field of medical instruments, and in particular, to an end-expiratory $CO_2$ guided tracheal intubation device.

TECHNICAL BACKGROUND

Tracheal intubation refers to the placement of a special endotracheal tube into the trachea through the glottis. This technique can provide the best conditions for airway patency, ventilation and oxygen supply, aspiration of the airway, and prevention of aspiration. Emergency tracheal intubation has become an important measure in the rescue of cardiopulmonary resuscitation and critically ill patients with respiratory dysfunction. Tracheal intubation is an important rescue technique commonly used in emergency work, which is one of the most widely used, most effective, and quickest means in respiratory management. It is a basic skill that medical staff must master skillfully, which plays a vital role in rescuing patients' lives and reducing mortality.

The existing tracheal intubation technique is using an intubation tube inserted into the larynx together with a speculum. The larynx is observed through the endoscope to find the trachea, and then the intubation tube is inserted into the larynx. However, in the process of intubation, pus will be secreted in the larynx and trachea, forming effusion in the larynx and trachea, causing visual impairment to the endoscope and affecting the insertion of the intubation tube.

SUMMARY OF THE INVENTION

An object of the present invention is to provide an end-expiratory $CO_2$ guided tracheal intubation device capable of determining the position of the tracheal intubation according to the end-expiratory $CO_2$ and clearing the fluid accumulated in the trachea in response to the shortcomings of the prior art.

To solve the above problems, the present invention provides an end-expiratory $CO_2$ guided tracheal intubation device, comprising: an intubation tube, an end-expiratory $CO_2$ catheter, a suction tube, an airbag, and an inflatable trachea; the end-expiratory $CO_2$ catheter partially penetrates a sidewall of the intubation tube, and one end thereof extends beyond an end of the intubation tube, and the other end is connected to an end-expiratory $CO_2$ sensor; the suction tube partially penetrates a sidewall of the intubation tube, and one end thereof extends beyond an end of the intubation tube, and the other end is connected to an air pump; the airbag is sleeved on the outer wall of the intubation tube; the inflatable trachea partially penetrates a sidewall of the intubation tube, one end thereof is connected to the airbag, and the other end is connected to the air supply device.

Optionally, the sidewall of the intubation tube is provided with an end-expiratory $CO_2$ catheter installation groove and a suction tube installation groove.

Optionally, the end-expiratory $CO_2$ catheter comprises a first end tube segment, a retractable first tube segment, and a first tail tube segment, which are connected in sequence; the first end tube segment is connected to the end-expiratory $CO_2$ sensor; the first tube segment is disposed in the end-expiratory $CO_2$ catheter installation groove and is sleeved with a first spring, and one end of the first spring is abutted on a first stop block provided on the first tail tube segment, and the other end thereof is abutted on an end wall of the end-expiratory $CO_2$ catheter installation groove; the first tail tube segment extends to the outside of the intubation tube.

Optionally, the suction tube comprises a second end tube segment, a retractable second tube segment, and a second tail tube segment, which are connected in sequence; the second end tube segment is connected to the air pump; the second tube segment is disposed in the suction tube installation groove and is sleeved with a second spring, and one end of the second spring is abutted on a second stop block provided on the send tail tube segment, and the other end thereof is abutted on an end wall of the suction tube installation groove; the second tail tube segment extends to the outside of the intubation tube.

Optionally, the connection between the airbag and the intubation tube is sealed.

The present invention provides an end-expiratory $CO_2$ guided tracheal intubation device, which uses the end-expiratory $CO_2$ sensor connected with the end-expiratory $CO_2$ catheter through the end-expiratory $CO_2$ catheter set in the intubation tube wall to detect the end-expiratory $CO_2$ in the patient's breath. According to the end-expiratory $CO_2$ data detected at different positions of the patient's larynx, and cooperating with the endoscope, the position of the endotracheal tube can be quickly and accurately determined. Through the suction tube provided in the inner wall of the intubation tube, the air pump connected to the suction tube is used to extract the effusion in the throat and trachea during the intubation process and after the intubation tube is in place, which is convenient for medical staff to use an endoscope for observation, and improves work efficiency.

The end-expiratory $CO_2$ guided tracheal intubation device provided by the present invention is provided with a retractable tube segment on the end-expiratory $CO_2$ catheter and a suction pipe, and a spring is sleeved on the outer wall thereof to allow it extend beyond the end face of the intubation tube. The tail tube segment can be retracted in time when it touches the patient's throat or trachea during tracheal intubation to prevent it from causing harm to the human body.

BRIEF DESCRIPTION OF THE DRAWINGS

In order to explain the technical solutions in the embodiments of the present invention or the prior art more clearly, the drawings used in the embodiments or the description of the prior art will be briefly introduced below. Obviously, the drawings in the following description are only some embodiments of the present invention. For those of ordinary skill in the art, other drawings can be obtained based on these drawings without creative efforts.

DESCRIPTION OF EMBODIMENTS

The specific implementation of the present invention will be further described in detail below with reference to the embodiments and the accompanying drawings. The following examples of the present invention herein are used to illustrate the present invention but are not intended to limit the scope of the present invention.

Example 1

Figure 1:
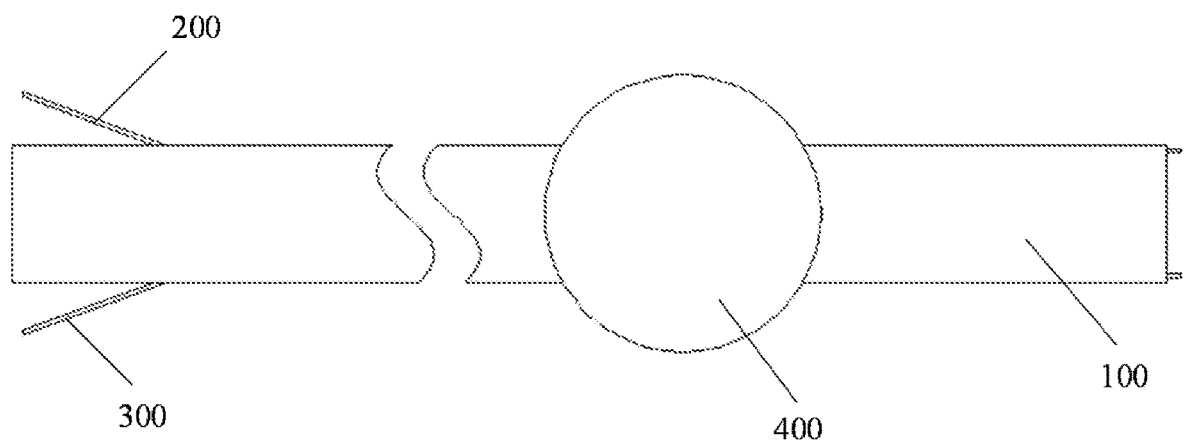
FIG. 1 is a schematic diagram of the overall structure of an end-expiratory $CO_2$ guided tracheal intubation device according to an embodiment of the present invention.
Figure 2:
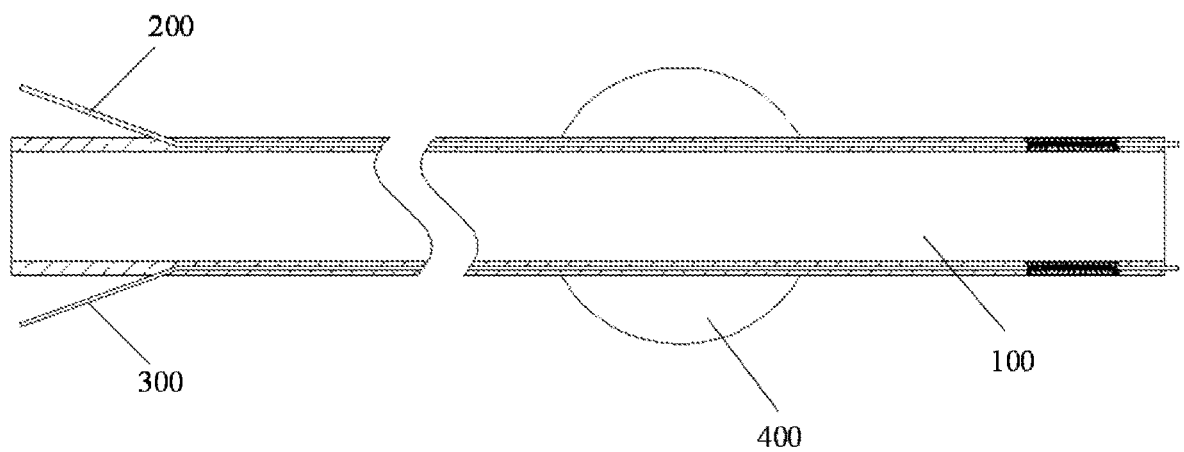
FIG. 2 is a schematic diagram of the internal structure of an end-expiratory $CO_2$ guided tracheal intubation device according to an embodiment of the present invention.

As shown in FIG. 1 and FIG. 2, an end-expiratory $CO_2$ guided tracheal intubation device according to an embodiment of the present invention includes an intubation tube 100, an end-expiratory $CO_2$ catheter 200, a suction tube 300, an airbag 400, and an inflatable tube 500. The end-expiratory $CO_2$ catheter 200 partially penetrates the sidewall of the intubation tube 100, and one end thereof extends beyond the end of the intubation tube 100, and the other end is connected to the end-expiratory $CO_2$ sensor; one end of the suction tube 300 partially penetrates the sidewall of the intubation tube 100, and the other end is connected to the air pump. In this embodiment, one end of the end-expiratory $CO_2$ catheter 200 enters the sidewall of the intubation tube 100 from somewhere near the left end of the intubation tube 100, and extends to the right in the sidewall, and penetrates the right end face of the intubation tube 100. The other end of the $CO_2$ catheter 200 is connected to an end-expiratory $CO_2$ sensor outside the intubation tube 100. One end of the suction tube 300 enters the sidewall of the intubation tube 100 from somewhere near the left end of the intubation tube 100, and extends to the right in the sidewall, and penetrates the right end face of the intubation tube 100. The other end of the suction tube 300 is connected to an air pump outside the intubation tube 100.

The number of end-expiratory $CO_2$ catheters 200 and suction tubes 300 provided in the sidewall of the intubation tube 100 may be determined according to needs. There may be one or multiple, which is not specifically limited in the embodiment of the present invention.

The positions of the end-expiratory $CO_2$ catheter 200 and the suction tube 300 entering the sidewall of the intubation tube 100 and the positions provided in the sidewall of the intubation tube 100 may be determined according to needs, for example, one or a plurality of end-expiratory $CO_2$ catheters 200 and suction tubes 300 are evenly arranged on the circumference of the cross-section of the intubation tube 100, which is not specifically limited in the embodiment of the present invention.

Figure 3:
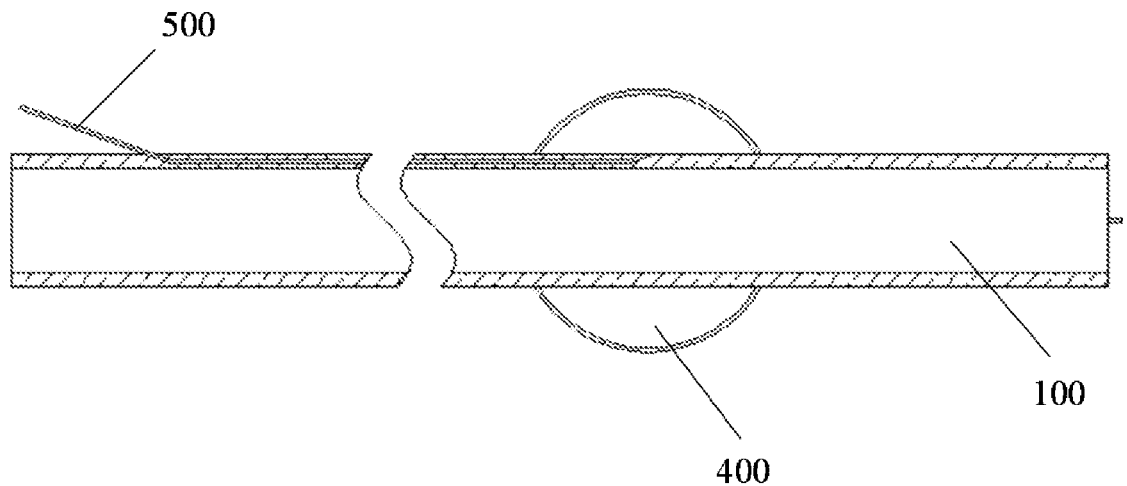
FIG. 3 is a schematic diagram of the internal structure of an end-expiratory $CO_2$ guided tracheal intubation device according to an embodiment of the present invention.
Figure 4:
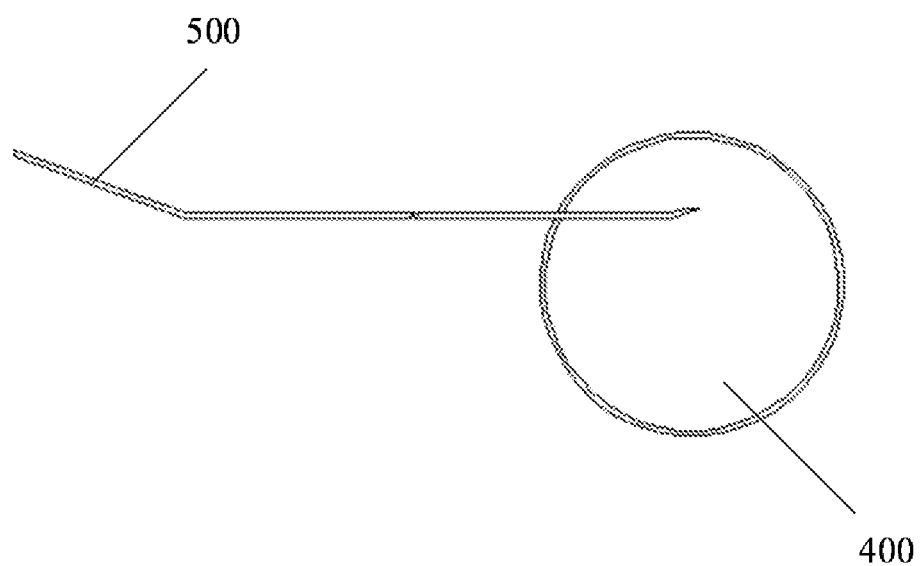
FIG. 4 is a schematic structural diagram of matching an airbag with an inflatable trachea of an end-expiratory $CO_2$ guided tracheal intubation device according to an embodiment of the present invention.

As shown in FIG. 3 and FIG. 4, the airbag 400 is sleeved on the outer wall of the intubation tube 100. The inflatable tube 500 partially penetrates the sidewall of the intubation tube 100, and one end thereof is connected to the airbag 400 and the other end is connected to the air supply device. In this embodiment, the airbag 400 is sleeved on the outer wall of the intubation tube 100, near the right end of the patient's trachea to be inserted into the intubation tube 100, and the connection with the outer wall of the intubation tube 100 is sealed. One end of the inflatable tube 500 enters the sidewall of the intubation tube 100 from somewhere near the left end of the intubation tube 100, and extends to the right in the sidewall to the outer wall section of the intubation tube 100 to which the airbag 400 is shelved, penetrating the sidewall or entering the airbag 400; the other end of the inflatable tube 500 is connected to the air pump outside the intubation tube 100. Before tracheal intubation, the airbag 400 is uninflated. When the tracheal intubation is completed and the intubation tube 100 is inserted into place, the air pump is started, and the airbag 400 is inflated through the inflatable tube 500 to inflate the airbag 400. After the airbag 400 is inflated, the intubation tube 100 is clamped, and at the same time, the inflation tube is clamped in the patient's trachea, thereby fixing the intubation tube 100 in the patient's trachea.

The position where the airbag 400 is sleeved on the outer wall of the intubation tube 100 can be determined according to requirements, which is not specifically limited in the embodiment of the present invention.

The position where the inflatable tube 500 enters the sidewall of the intubation tube 100 and the position provided in the sidewall of the intubation tube 100 can be determined according to requirements, which is not specifically limited in this embodiment of the present invention.

In one embodiment, to ensure the safety of the patient, the intubation tube 100 is made of medical PVC material, which is not specifically limited in the embodiment of the present invention.

When the present invention is used specifically, the left end of the end-expiratory $CO_2$ catheter 200 is connected to the end-expiratory $CO_2$ sensor outside the intubation tube 100; the left end of the suction tube 300 is connected to the air pump outside the intubation tube 100; then the endoscope is inserted into the lumen of the intubation tube 100. The right end of the intubation tube 100 is entered into the patient's throat with the airbag 410 sleeved on the sidewall of the intubation tube 100. The right end of the end-expiratory $CO_2$ catheter 200 passing through the right end face of the intubation tube 100 transmits the patient's exhaled gas to the end-expiratory $CO_2$ sensor and detects the end-expiratory $CO_2$. Adjust the position of the right port of the intubation tube 100 in the throat, and observe the end-expiratory $CO_2$ data at different positions. According to the end-expiratory $CO_2$ data of each position, determining the position where the intubation tube 100 is to be inserted into the trachea, and at the same time observing the throat through the endoscope in the inner cavity of the intubation tube 100, and fine-tune the position of the intubation tube 100 so that the intubation tube 100 is aligned with the trachea, and the intubation tube 100 is inserted into the trachea of the patient. After inserting the intubation tube 100 into place, starting the air pump outside the intubation tube 100, inflating the airbag 400 through the inflatable tube 500 connected to the air pump, expanding the airbag 400, then clamp the intubation tube 100, and locking the airbag 400 in the patient's trachea, so that the intubation tube 100 is fixed in the trachea of the patient.

During the tracheal intubation and after the intubation is fixed in place, if there is effusion (for example, pus secreted by the throat or trachea) in the larynx or trachea of the patient observed by the endoscope located in the lumen of the intubation, starting an air pump, which is connected to the suction tube 300 and is located outside the intubation tube 100, to draw out the effusion in the throat or trachea through the suction tube 300.

When the intubation tube 100 is to be taken out of the patient's trachea, the airbag 400 is deflated by an air pump, the air in the airbag 400 is evacuated, and then the intubation tube 100 is pulled out of the patient's trachea.

The present invention provides an end-expiratory $CO_2$ guided tracheal intubation device, which uses the end-expiratory $CO_2$ sensor connected with the end-expiratory $CO_2$ catheter to detect the end-expiratory $CO_2$ in the patient's breath through the end-expiratory $CO_2$ catheter set in the intubation tube wall. According to the end-expiratory $CO_2$ data detected at different positions of the patient's larynx, and cooperating with the endoscope, the position of the endotracheal tube can be quickly and accurately determined. Through the suction tube provided in the inner wall of the intubation tube, the air pump connected to the suction tube is used to extract the effusion in the throat and trachea during the intubation process and after the intubation tube is in place, which is convenient for medical staff to use an endoscope for observation, and improves work efficiency.

Example 2

Figure 5:
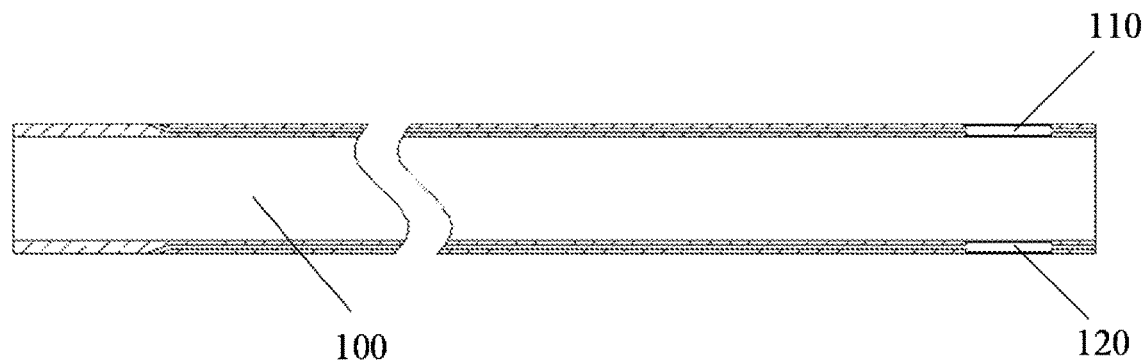
FIG. 5 is a schematic diagram of the internal structure of an intubation tube of an end-expiratory $CO_2$ guided tracheal intubation device according to an embodiment of the present invention.
Figure 6:
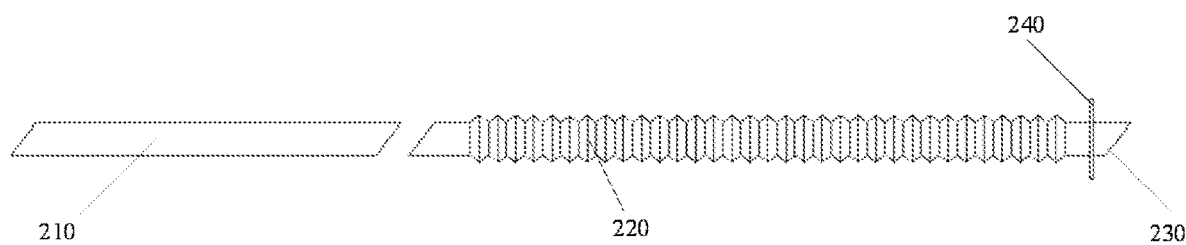
FIG. 6 is a schematic structural diagram of an end-expiratory $CO_2$ catheter of an end-expiratory $CO_2$ guided tracheal intubation device according to an embodiment of the present invention.
Figure 7:
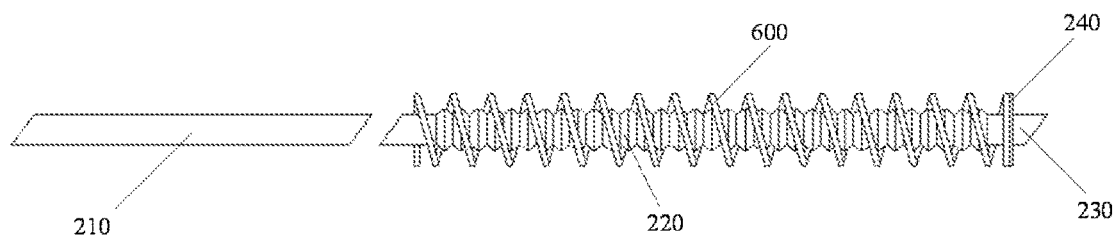
FIG. 7 is a schematic structural diagram of matching an end-expiratory $CO_2$ catheter with a first spring in an end-expiratory $CO_2$ guided tracheal intubation device according to an embodiment of the present invention.

The similarities between this example and example 1 will not be described again. As shown in FIG. 5 to FIG. 7, an end-expiratory $CO_2$ catheter installation groove 110 is provided in a sidewall of the intubation tube 100. The end-expiratory $CO_2$ catheter 200 includes a first end tube segment 210, a first tube segment 220, and a first end tube segment 230, which are connected in sequence; the first end tube segment 210 is connected to the end-expiratory $CO_2$ sensor; the first tube segment 220 is provided in end-expiratory $CO_2$ catheter installation groove 110, and sleeved with a first spring 600. One end of the first spring 600 is abutted on the first stop block 240 provided on the first tail tube segment 230, and the other end thereof is abutted on an end wall of the end-expiratory $CO_2$ catheter installation groove; the first tail tube segment 230 extends to the outside of the intubation tube 100. In this embodiment, the right end of the intubation tube 100 is inserted into the trachea of the patient, and the end-expiratory $CO_2$ catheter installation groove 110 is disposed in a sidewall near the right end of the intubation tube 100. The end-expiratory $CO_2$ catheter 200 comprises, from left to right, a first end tube segment 210, a retractable first tube segment 220, and a first tail tube segment 230; the left end of the first end tube segment 210 is connected to the end-expiratory $CO_2$ sensor outside the intubation tube 100, and the retractable first section 220 is located in the end-expiratory $CO_2$ catheter installation groove 110, and a first spring 600 is sleeved on the outer wall thereof. The left end of the first spring 600 is abutted on the left end wall of the end-expiratory $CO_2$ catheter installation groove 110, and the right end thereof is abutted on the first stop block 240 provided on the first tail tube segment 230 so that the first spring 600 is in a compressed state. The right end of the first tail tube segment 230 penetrates the right end surface of the intubation tube 100 and extends beyond the right end surface of the intubation tube 100.

Figure 8:
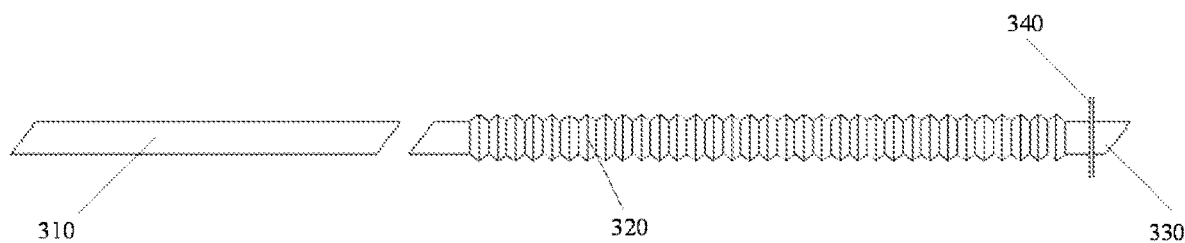
FIG. 8 is a schematic structural diagram of a suction tube of an end-expiratory $CO_2$ guided tracheal intubation device according to an embodiment of the present invention.
Figure 9:
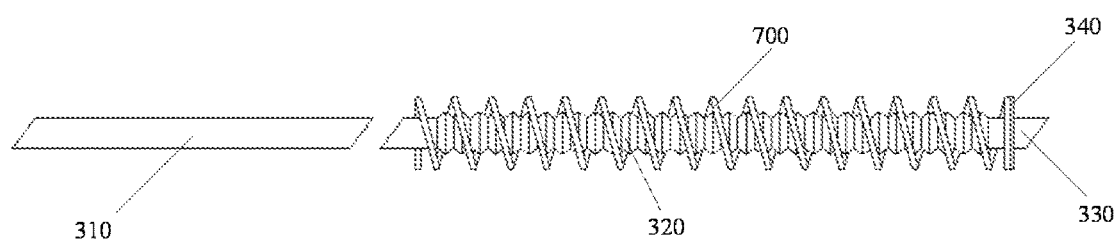
FIG. 9 is a schematic structural diagram of matching the suction tube with a second spring of the end-expiratory $CO_2$ guided tracheal intubation device according to an embodiment of the present invention.

Based on example 1, as shown in FIG. 5, FIG. 8, and FIG. 9, the sidewall of the intubation tube 100 is provided with a suction tube installation groove 120. The suction tube 300 includes a second end tube segment 310, a retractable second tube segment 320, and a second tail tube segment 330, which are connected in sequence; the second end tube segment 310 is connected to the air pump outside the intubation tube 100; the retractable second tube segment 320 is disposed in the suction tube installation groove 120 and is sleeved with a second spring 700. One end of the second spring 700 is abutted on the second stop block 340 provided on the second tail tube segment 330, and the other end thereof is abutted on an end wall of the end-expiratory $CO_2$ catheter installation groove 120; the second tail tube segment 330 extends to the outside of the intubation tube 100. In this embodiment, the right end of the intubation tube 100 is inserted into the trachea of the patient, and the suction tube mounting groove 120 is disposed in a sidewall near the right end of the intubation tube 100. From left to right, the suction tube 300 comprises a second end tube segment 310, a retractable second tube segment 320, and a second tail tube segment 330. The left end of the second end tube segment 310 is connected to the air pump outside the intubation tube 100, and the retractable second tube segment 320 is located in the suction tube installation groove 120, and a second spring 700 is sleeved on the outer wall thereof. The left end of the second spring 700 is abutted on the left end wall of the suction tube mounting groove 120, and the right end is abutted on the second limit block 340 provided on the second tail tube segment 330 so that the second spring 700 is in a compressed state. The right end of the second tail tube segment 330 penetrates the right end face of the intubation tube 100 and extends beyond the right end face of the intubation tube 100.

When a plurality of end-expiratory $CO_2$ catheters 200 and/or suction tubes 300 are provided in the sidewall of the intubation tube 100, a corresponding number of end-expiratory $CO_2$ catheter installation grooves 110 and suction tube installation grooves 120 are provided in the sidewall of the intubation tube 100.

The positions of the end-expiratory $CO_2$ catheter installation groove 110 and the suction tube installation groove 120 on the sidewall of the intubation tube 100 may be determined according to requirements, which are not specifically limited in this embodiment of the present invention.

The lengths of the first tail tube segment 230 of the end-expiratory $CO_2$ catheter 200 and the second tail tube segment 330 of the suction tube 300 extending to the outside of the end face of the intubation tube 100 can be determined according to requirements, which are not specifically limited in this embodiment of the present invention.

The process of tracheal intubation in this embodiment is the same as that of example 1 and will not be described again. In the present embodiment, when the intubation tube 100 is inserted into the patient's throat or trachea, when the end of the first tail tube segment 230 of the end-expiratory $CO_2$ catheter 200 extending outside the right end face of the intubation tube 100 touches human tissue (for example, on the throat or trachea), due to the force, it moves to the inside of the intubation tube and transmits the force to the first tube segment 220, so that the first tube segment 220 is contracted inward after being stressed, preventing the rigid contact between the first tail tube segment 230 and the human body tissues, and reducing the damage to human tissues. At the same time, the first limit block 240 disposed on the first tail tube segment 230 moves with the first tail tube segment 230, so the first spring 600 abutted on the first limit block 240 is compressed. When the end of the first tail tube segment 230 is no longer in contact with human tissue, the compressed first spring 600 is reset and drives the first tube segment 220 to extend, so that the first tail tube segment 230 returns to its original position (extending outside the right end wall of the intubation tube 100).

During the insertion of the intubation tube 100 into the patient's throat or trachea, when the end of the second tail tube segment 330 of the suction tube 300 that extends beyond the right end face of the intubation tube 100 touches human tissue, the second tube segment 320 contracts. The process of resetting under the action of the second spring 700 is similar to the process of the end-expiratory $CO_2$ catheter 200 described above, and will not be described again.

The end-expiratory $CO_2$ guided tracheal intubation device provided by the present invention is provided with a retractable tube segment on the end-expiratory $CO_2$ catheter and the suction tube, and a spring is sleeved on the outer wall thereof, so that the tail tube segment extending beyond the end face of the intubation tube can be retracted when it touches the patient's throat or trachea during tracheal intubation to prevent it from causing harm to the human body.

In the description of the present invention, it should be noted that the terms "installed", "connected with", and "connected to" should be understood in a broad sense unless otherwise specified and limited. For example, it can be a fixed connection, a detachable connection, or an integrated connection; it can be a mechanical connection or an electrical connection; it can be a direct connection or an indirect connection through an intermediate medium, and it also can be the internal connection of two components. For those of ordinary skill in the art, the specific meaning of the above terms in the invention can be understood in specific circumstances, and should not be understood as a limitation of the invention.

The above embodiments are only used to illustrate the present invention but are not intended to limit the present invention. Although the present invention has been described in detail with reference to the embodiments, those of ordinary skill in the art should understand that various combinations, modifications, or equivalent replacements of the technical solutions of the present invention shall not depart from the spirit and scope of the technical solutions of the present invention, and shall all fall within the scope of the claims of the present invention.

It should be noted that the terminology used herein is to describe particular embodiments only and is not intended to be limiting of the exemplary embodiments according to the present application. As used herein, the singular forms are intended to include the plural forms as well, unless the context indicates otherwise. It will be further understood that the terms "comprises" or "includes" when used in this specification, specify the presence of stated features, steps, operations, elements, components, and/or combinations thereof.

In the present invention, terms such as "up", "down", "left", "right", "front", "rear", "vertical", "horizontal", "side", "bottom" that indicating the orientation or positional relationship are based on the orientation or positional relationship shown in the Figures, and are only relational terms determined for the convenience of describing the structural relationship of each component or element of the present invention, and do not specifically refer to any component or element in the present invention, and should not be understood as the limitations of the present invention.

The above descriptions are merely preferred embodiments of the present invention and are not intended to limit the present invention. For those skilled in the art, the present invention may have various modifications and changes. Any modification, equivalent replacement, and improvement made under the spirit and principle of the present invention shall be included in the protection scope of the present invention.

What is claimed is:

1. An end-expiratory $CO_2$ guided tracheal intubation device, comprising an intubation tube, an end-expiratory $CO_2$ catheter, a suction tube, an airbag, and an inflation tube, wherein:
   the end-expiratory $CO_2$ catheter partially penetrates a sidewall of the intubation tube, and one end of the end-expiratory $CO_2$ catheter extends beyond an end of the intubation tube, and the other end of the end-expiratory $CO_2$ catheter is connected to an end-expiratory $CO_2$ sensor;
   the suction tube partially penetrates the sidewall of the intubation tube, and one end of the suction tube extends beyond the end of the intubation tube, and the other end of the suction tube is connected to an air pump;
   the airbag is sleeved on an outer wall of the intubation tube (100);
   the inflation tube partially penetrates the sidewall of the intubation tube, and one end of the inflation tube is connected to the airbag and the other end of the inflation tube is connected to an air supply device;
   the sidewall of the intubation tube is provided with an end-expiratory $CO_2$ catheter installation groove and a suction tube installation groove;
   the end-expiratory $CO_2$ catheter comprises a first end tube segment, a retractable first tube segment and a first tail tube segment, which are connected in sequence; the first end tube segment is connected to the end-expiratory $CO_2$ sensor; the first tube segment is disposed in the end-expiratory $CO_2$ catheter installation groove, and is sleeved with a first spring, one end of the first spring is abutted on a first stop block provided on the first tail tube segment, and the other end of the first spring is abutted on an end wall of the end-expiratory $CO_2$ catheter installation groove; the first tail tube segment extends to the outside of the intubation tube;
   the suction tube comprises a second end tube segment, a retractable second tube segment and the second tail tube segment, which are connected in sequence; the second end tube segment is connected to the air pump; the second tube segment is disposed in the suction tube installation groove, and is sleeved with a second spring;
   one end of the second spring is abutted on a second stop block provided on the send tail tube segment, and the other end of the second spring is abutted on an end wall of the suction tube installation groove; the second tail tube segment extends to the outside of the intubation tube.

2. The end-expiratory $CO_2$ guided tracheal intubation device according to claim 1, wherein the connection between the airbag and the intubation tube is sealed.

* * * * *